United States Patent [19]

Messmer et al.

[11] Patent Number: 4,697,013
[45] Date of Patent: * Sep. 29, 1987

[54] CONDENSED AS-TRIAZINE DERIVATIVES

[75] Inventors: András Messmer; Sándor Bátori; György Hajós; Pál Benkó; László Pallos; Lujza Petöcz; Grasser Katalin; Ibolya Kosóczky, all of Budapest, Hungary

[73] Assignee: Egyt Gyogyszervegyeszeti Gyar, Budapest, Hungary

[ * ] Notice: The portion of the term of this patent subsequent to Dec. 6, 2000 has been disclaimed.

[21] Appl. No.: 652,613

[22] Filed: Sep. 20, 1984

[30] Foreign Application Priority Data

Sep. 20, 1983 [HU] Hungary ............... 2251/3241/83

[51] Int. Cl.[4] ............................................. C07D 253/08
[52] U.S. Cl. ................................................... 544/183
[58] Field of Search ........................ 544/183; 514/243

[56] References Cited

U.S. PATENT DOCUMENTS 4,419,355 12/1983 Kosoczky et al. ............... 544/183

FOREIGN PATENT DOCUMENTS 3218386 10/1983 Fed. Rep. of Germany.

OTHER PUBLICATIONS

Kakehi et al, Japan-Chemistry Letters pp. 413–414 (1976).

Primary Examiner—John M. Ford
Attorney, Agent, or Firm—Keil & Weinkauf

[57] ABSTRACT

A one step process for the preparation of compounds having antidepressant activity of the formula I

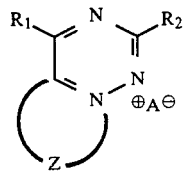

and isomers thereof, wherein $R_1$, $R_2$, Z and $A^-$ have the meanings indicated in the claims, which process comprises: heating a compound of the formula II

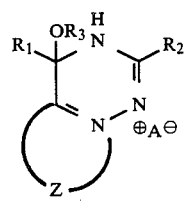

wherein Z, $A^-$, $R_1$ and $R_2$ have the meanings set out in the claims and $R_3$ stands for hydrogen or $C_{1-4}$ alkyl, in the presence of a dehydrating agent to split off a compound of the formula $R_3OH$. The invention is also directed to compounds of the formula I, wherein $R_2$ is halogen and to compositions containing a compound of the formula I which exhibit antidepressant activity.

3 Claims, No Drawings

CONDENSED AS-TRIAZINE DERIVATIVES

This invention relates to a new and improved process for the preparation of partly new condensed as-triazine derivatives.

According to an aspect of the present invention there is provided a process for the preparation of compounds of the general Formula I

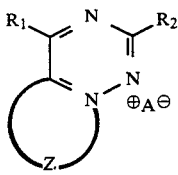
/I/ and isomers thereof wherein $R_1$ is $C_{1-10}$ alkyl or phenyl or naphthyl, the two latter groups being optionally substituted by one or more halogen, nitro, amino, hydroxy, $C_{1-4}$ alkyl and/or $C_{1-4}$ alkoxy substituent(s);

$R_2$ represents hydrogen, halogen, $C_{1-14}$ alkyl or phenyl or naphthyl, the two latter groups being optionally substituted by one or more halogen, nitro, amino, hydroxy, $C_{1-4}$ alkyl and/or $C_{1-4}$ alkoxy substituent(s);

Z is buta-1,3-dienyl or a group of the Formula (a)

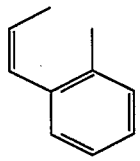
/a/ or /b/

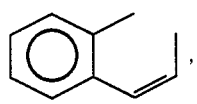
/b/ and $A^-$ is an anion, which comprises (a) removing from a compound of the general Formula II

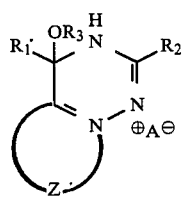
/II/

(wherein Z, $A^-$, $R_1$ and $R_2$ are as stated above and $R_3$ stands for hydrogen or $C_{1-4}$ alkyl) a compound of the general Formula $R_3OH$; or (b) reacting a "Zwitterion" compound of the general Formula III

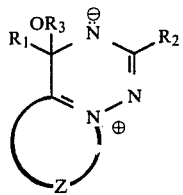
/III/

(wherein $R_1$, $R_2$, $R_3$ and Z are as stated above) with an acid of the general Formula IV $$H^+A^- \qquad (IV)$$

(wherein $A^-$ is as stated above); or (c) for the preparation of compounds of the general Formula I, wherein $R_2$ stands for halogen (and $R_1$, Z and $A^-$ are as stated above)

($c_1$) reacting a compound of the general Formula V

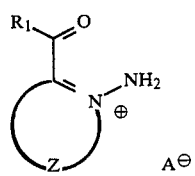
/V/

(wherein $R_1$, Z and $A^-$ are as stated above) with urea and a halogenating agent having dehydrating effect and reacting the product thus obtained with an acid of the general Formula IV; or ($c_2$) reacting a compound of the general Formula VI

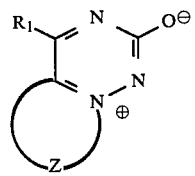
/VI/

(wherein $R_1$ and Z are as stated above) with a halogenating agent and, if desired, reacting the product thus obtained with an acid of the general Formula IV (wherein $A^-$ is as stated above)

and, if desired, separating a compound of the general Formula I thus obtained into the isomers thereof and/or, if desired, exchanging an $A^-$ anion for an other $A^-$ anion.

The term "alkyl" used throughout the specification relates to straight or branched chain alkyl process (e.g. methyl, ethyl, n-propyl, isopropyl, tert. butyl etc.). The said alkyl groups have preferably 1–6, particularly advantageously 1–4 carbon atoms. The term "alkoxy group" relates to straight or branched chain alkoxy groups (e.g. methoxy, ethoxy, isopropoxy etc.). The term "halogen" encompasses the fluorine, chlorine, bromine and iodine atoms.

$A^-$ stands preferably for a pharmaceutically acceptable inorganic or organic anion, e.g. a halide anion—preferably chloride, bromide or iodide—or perchlorate, methane sulfonate, ethane sulfonate or p-toluene sulfonate.

According to a preferred feature of the present invention compounds of the general Formula I are prepared, in which Z is a group of the general Formula (b). According to a further preferred feature of the present invention compounds of the general Formula I are prepared in which $R_1$ stands for phenyl optionally substituted by halogen in position 4, preferably for 4-chlorophenyl. According to a still further preferable feature of the present invention there are prepared compounds of the general Formula I, wherein $R_2$ is hydrogen, halogen, methyl or phenyl.

According to a particularly preferred feature of the present invention 1-(4-chloro-phenyl)-as-triazino[6,1-a]isoquinolinium-bromide is prepared.

The compounds of the general Formula I, wherein $R_2$ is halogen, are new. The other compounds of the general Formula are known (DOS No. 3,218,386).

According to a further aspect of the present invention there are provided new compounds of the general Formula I (wherein $R_2$ is halogen and $R_1$, Z and $A^-$ are as stated above). The said new compounds of the present invention possess useful pharmacological properties and exhibit first of all antidepressant effect. Compounds of the general Formula I, wherein $R_2$ is chlorine, have particularly useful pharmacological effect.

According to method (a) of the process of the present invention a compound of the general Formula $R_3OH$ is split off from a starting material of the general Formula II.

From starting materials of the general Formula II, in which $R_3$ is hydrogen, water is split off. The reaction is carried out in anhydrous medium, in the presence of a dehydrating agent, under heating. As dehydrating agent an inorganic acid anhydride—preferably phosphorous pentoxide, phosphorous oxychloride, phosphorous pentachloride or polyphosphoric acid—or an organic carboxylic acid anhydride—preferably acetic anhydride or propionic acid anhydride—may be used. It is particularly advantageous to use phosphorous pentoxide as dehydrating agent.

Dehydration may be carried out in the melt or in an inert anhydrous organic solvent as medium. The excess of the dehydrating agent may also play the role of the reaction medium. As anhydrous inert organic solvent e.g. halogenated hydrocarbons (such as chloroform, carbon tetrachloride or chlorobenzene), aromatic hydrocarbons (e.g. xylene, toluene or benzene), dialkyl amides (e.g. dimethyl formamide), dialkyl sulfoxides (e.g. dimethyl sulfoxide), cyclic ethers (e.g. tetrahydrofurane or dioxane), aliphatic ethers (e.g. diethyl ether), other hydrocarbons (e.g. n-hexane or petrol) or acetonitrile or a mixture thereof may be used. The reaction is carried out under heating, preferably at a temperature above 80 C.°, particularly at 100°-120 C.°. The reaction may be carried out at atmospheric pressure or in vacuo. In the latter case the reaction can be carried out at a lower temperature. The reaction takes place within some hours.

From starting materials of the general Formula II, wherein $R_3$ is $C_{1-4}$ alkyl, an alkanol having 1-4 carbon atoms is split off. It is preferred to use as starting material a compound of the general Formula II, wherein $R_3$ is methyl. The alkanol is preferably split off under heating, in the melt. One may preferably work at 80°-150 C.°.

In the said reactions only solvents with such a basicity can be used which do not bind the anion.

The reaction mixture may be worked up by methods known per se (e.g. extraction, evaporation, filtration etc.).

The starting materials of the general Formula II are novel and the transformation thereof into compounds of the general Formula I is a reaction of a new type. In the case of condensed systems comprising a quinolinium or isoquinolinium ring it was not known so far to form the aromatic structure by removing a hydroxy or alkoxy group from position 1.

According to method (b) of the process of the present invention a "Zwitterion" type compound of the general Formula III is reacted with an acid of the general Formula IV. The reaction is carried out in an anhydrous medium. As reaction medium preferably such solvents may be used in which the acid comprising the $A^-$ anion is soluble. The solvents enumerated in connection with method (a) may be used and acetonitrile may be particularly preferably applied. The reaction may be carried out at a temperature in the range of 0°-150 C.°, preferably at 15°-35 C.°.

The starting materials of the general Formula III are novel compounds and the conversion thereof into compounds of the general Formula I is a reaction of a new type.

The reaction mixture may be worked up by methods known per se.

According to process (c) compounds of the general Formula I can be prepared in which $R_2$ stands for halogen. The said process can be carried out by two variants.

According to method ($c_1$) a starting material of the general Formula V is reacted with urea and a halogenating agent having dehydrating effect and, if desired, the product thus obtained is subjected to anion exchange by reacting the same with an acid comprising the anion to be introduced. As halogenating agent inorganic acid halides, preferably phosphorous oxychloride, phosphorous oxybromide, thionyl chloride or phosphorous pentachloride may be used. The reaction may be carried out in any suitable inert organic solvent. As reaction medium preferably solvents having a higher boiling point may be used (e.g. acetonitrile, dimethyl formamide, dichlorobenzene or quinoline, preferably acetonitrile). The reaction may be carried out preferably at elevated temperature—particularly at 100°-250 C.°, advantageously at 110°-180 C.°.

According to method ($c_2$) of the process of the present invention a compound of the general Formula VI is reacted with a halogenating agent and, if desired, the product thus obtained is reacted with an acid comprising the desired anion. As halogenating agent preferably inorganic acid halides (e.g. phosphorous oxychloride, phosphorous oxybromide, thionyl chloride or phosphorous pentachloride) may be used. The excess of the halogenating agent or an inert organic solvent may act as reaction medium. The reaction may be carried out under heating, preferably at 100°-250 C.°.

The compound of the general Formula I may be separated into its isomers by methods known per se, if desired.

In the compound of the general Formula I the anion may be exchanged for an other anion by methods known per se, if desired. Thus e.g. a compound of the general Formula I comprising a chloride ion as $A^-$ may be converted into the corresponding compound of the general Formula I comprising a perchlorate ion as A⁻ by treatment with perchloric acid. Compounds of the general Formula I comprising a bromide ion as A⁻ may be prepared from compounds of the general Formula I containing an other anion—e.g. a perchlorate ion—as A⁻ by reacting with tetrabutyl ammonium bromide.

The starting materials may be prepared as follows:

The starting materials of the general Formula II, III and VI are new compounds which are claimed in the Hungarian patent application Ser. Nos. 3242/83 and 8243/83. The starting materials of the general Formula V are known (DOS No. 3,128,386).

The said new starting materials can be prepared by subjecting a compound of the general Formula V to cyclisation and reacting the product thus obtained with water or an alkali metal alcoholate or treating the same with an inorganic base in aqueous medium.

The advantage of the process of the present invention is that the compounds of the general Formula I can be prepared by a one-step method with excellent yields. On the other hand, according to DOS No. 3,128,386 the compounds of the general Formula I (wherein $R_2$ is other than halogen of $R_1$, Z and A⁻ are as stated above) are prepared by a lengthy multi-step synthesis with lower yields than achievable by the present invention.

According to a further feature of the present invention there are provided pharmaceutical compositions comprising as active ingredient at least one compound of the general Formula I (wherein $R_2$ stands for halogen and $R_1$, A⁻ and Z are as stated above) in admixture with suitable inert pharmaceutical carriers and/or excipients.

The said pharmacetical compositions may be prepared by methods of pharmaceutical industry known per se.

The compositions may be solid (e.g. tablets, capsules, coated pills, dragées), semi-solid (e.g. ointments) or liquid (e.g. solutions, suspensions, emulsions). The compositions may be finished in forms suitable for oral or parenteral administration.

The pharmaceutical compositions of the present invention may contain carriers. The said carriers may be solid diluents, fillers, sterile aqueous solutions or non-toxic organic solvents. The tablets suitable for oral administration may comprise sweetening agents and/or other auxiliary agents (e.g. starch, preferably potato starch), binding agents (e.g. polyvinyl pyrrolidone, gelatine), sliding agents (e.g. magnesium stearate, sodium lauryl sulfate or talc), or other additives (e.g. sodium citrate, calcium carbonate, dicalcium phosphate, etc.). The aqueous suspensions and elixirs suitable for oral administration may further comprise flavourants, dyes, emulsifiers, diluents (e.g. water, ethanol, propylene glycol or glycerol etc.).

The parenteral compositions may comprise pharmaceutically acceptable solvents (e.g. sesame oil, peanut oil, aqueous propylene glycol, dimethyl formamide, etc.) or water when water-soluble active ingredients are used. The aqueous solutions may be treated with a buffer solution or made isotonic with the aid of a liquid diluent (e.g. sodium chloride or glucose). The aqueous solutions are particularly suitable for intravenous, intramuscular or intraperitoneal administration. The sterile aqueous solutions are prepared by methods known per se.

The daily dosage of the active ingredient of the general Formula I may be varied within wide ranges and depends on several factors, particularly the efficiency of the active ingredient used, the method of administration and the state of the patient.

Further details of the present invention are to be found in the following Examples without limiting the scope of protection to the said Examples.

EXAMPLE 1

Preparation of 3-chloro-1-(4-chloro-phenyl)-as-triazino[6,1-a]isoquinolinium-perchlorate 1 g (0,0033 mole) of 1-(4-chloro-phenyl)-as-triazino[6,1-a]isoquinoline-5-ium-3-olate are dissolved in phosphorus oxychloride under heating to boiling whereupon the excess of phosphorous oxychloride is removed, the residue is suspended in acetic acid and 0.5 ml of 70% perchloric acid are added. Thus 1 g of the aimed compound is obtained in the form of yellow crystals. Yield 72%. Mp.: 292°–294 C.°.

EXAMPLE 2

Preparation of 3-chloro-1-(4-chloro-phenyl)-as-triazino[6,1-a]isoquinolinium-perchlorate A mixture of 1.9 g (0.02 mole) of N-amino-1-(4-chloro-phenyl)-isoquinolylketone-perchlorate, 3 g (0.05 mole) of urea, 15 ml of phosphorous oxychloride and 30 ml of acetonitrile is heated to boiling. The solution is evaporated and to the residue 25 ml of 70% perchloric acid are added. Thus 1.6 g of the aimed compound are obtained, yield: 76%. Mp.: 290 C.° (from a mixture of acetonitrile and ether).

EXAMPLE 3

Preparation of 4-phenyl-as-triazino[1,6-a]quinolinium-perchlorate 2.58 g (0.01 mole) of 4-phenyl-4-hydroxy-as-triazino[1,6-a]quinolin-11-ium-3(4H)-ide are reacted with 1 ml of 70% perchloric acid in 8 ml of acetonitrile. After the product has dissolved, ether is added. Thus 3.1 g of the aimed compound are obtained in the form of needle crystals, yield: 90%. Mp.: 320°–321 C.°.

EXAMPLE 4

Preparation of 1-phenyl-as-triazino[6,1-a]isoquinolinium-perchlorate

A mixture of 7.5 g (0,02 mole) of 1-phenyl-1-hydroxy-1,2-dihydro-as-triazino[6,1-a]isoquinolinium-perchlorate and phosphorous pentoxide is heated at 100 C.° for 8 hours. Thus 7.1 g of the aimed compound are obtained, yield 100%. Mp.: 245°–246 C.°.

EXAMPLE 5

Preparation of 4-(4-chloro-phenyl)-as-triazino[1,6-a]quinolinium-perchlorate 2.58 g (0,01 mole) of 4-(4-chloro-phenyl)-4-hydroxy-as-triazino[1,6-a]quinolin-11-ium-3-(4H)-ide are reacted with 1 ml of 70% perchloric acid in 8 ml of acetonitrile. After the starting material has dissolved, ether is added. Thus 3.0 g of the desired compound are obtained in the form of needle crystals. Yield 85%. Mp.: 293 C.°.

EXAMPLE 6

Preparation of 4-(4-fluoro-phenyl)-as-triazino[1,6-a]quinolinium-perchlorate 4-(4-fluoro-phenyl)-4-hydroxy-3,4-dihydro-as-triazino[1,6-a]quinolinium-chloride is reacted with 70% perchloric acid in acetonitrile. The desired compound is obtained in a yield of 89%, mp.: 282 C.°.

EXAMPLE 7

Preparation of 1,3-diphenyl-pyrido[2,1-f]-as-triazinium-bromide

One proceeds according to Example 3 except that 1,3-diphenyl-1-hydroxy-pyrido[2,1-f]-as-triazinium-2-(1H)-ide is used as starting material. The 1,3-diphenyl-pyrido[2,1-f]-as-triazinium-perchlorate thus obtained is treated with tetrabutyl ammonium bromide. The desired compound is obtained with a yield of 98%, mp.: 279°–280 C.°.

EXAMPLE 8

Preparation of 1-phenyl-3-methyl-pyrido[2,1-f]-as-triazinium-perchlorate

One proceeds according to Example 6 except that 1-phenyl-1-hydroxy-3-methyl-1,2-dihydro-pyrido[2,1-f]-as-triazinium-chloride is used as starting material. The aimed compound is obtained in a yield of 96%. Mp.: 271 C.°.

EXAMPLE 9

Preparation of 1-(4-chloro-phenyl)-as-triazino[6,1-a]isoquinolinium-perchlorate 1-(4-chloro-phenyl)-1-methoxy-1,2-dihydro-as-triazino[6,1-a]isoquinolinium-perchlorate is heated at a temperature above 100 C.°. Methanol is split off and the aimed compound is obtained in a yield of 90%, mp.: 239°–240 C.°.

EXAMPLE 10

Preparation of 1-(4-chloro-phenyl)-as-triazino[6,1-a]isoquinolinium-bromide 3.91 g (0.01 mole) of 1-(4-chloro-phenyl)-as-triazino[6,1-a]isoquinolinium-perchlorate are reacted with 3.12 g of tetrabutyl ammonium bromide in 8 ml of acetonitrile. The aimed compound is precipitated by adding ether. Thus 3.26 g of the aimed compound are obtained, yield 90%, mp.: 264°–265 C.°.

What we claim is:

1. A compound of the formula I

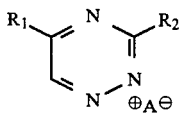

and isomers thereof wherein
$R_1$ is $C_{1-10}$ alkyl or phenyl or naphthyl, the two latter groups being optionally substituted by one or more halogen, nitro, amino, hydroxy, $C_{1-4}$ alkyl and/or $C_{1-4}$ alkoxy substituents is halogen,
Z is buta-1,3-dienyl or a group of the formula a

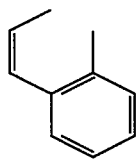

or b

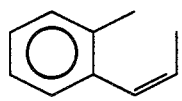

and
$A^-$ is an anion.

2. A compound of the formula I as defined in claim 1, wherein $R_2$ is chlorine.

3. 3-Chloro-1-(4-chloro-phenyl)-as-triazino[6,1-a 7-isoquinolinium-perchlorate.

* * * * *